(12) United States Patent
Seto et al.

(10) Patent No.: US 8,308,745 B2
(45) Date of Patent: Nov. 13, 2012

(54) FLUID JET DEVICE

(75) Inventors: Takeshl Seto, Chofu (JP); Kazuyoshi Takayama, Sendai (JP)

(73) Assignee: Seiko Epson Corporation, Tokyo (JP)

( * ) Notice: Subject to any disclaimer, the term of this patent is extended or adjusted under 35 U.S.C. 154(b) by 569 days.

(21) Appl. No.: 12/184,646

(22) Filed: Aug. 1, 2008

(65) Prior Publication Data
US 2009/0043320 A1   Feb. 12, 2009

(30) Foreign Application Priority Data

Aug. 10, 2007   (JP) ................................. 2007-208960

(51) Int. Cl.
    *A61B 17/3203* (2006.01)
(52) U.S. Cl. ...................................................... 606/167
(58) Field of Classification Search ............... 433/80;
    601/154, 162; 604/19, 68–70, 22, 23, 24,
    604/26; 606/159, 167, 169, 170; 15/22.2;
    451/40, 75, 102; 29/81.08; 83/177
    See application file for complete search history.

(56) References Cited

U.S. PATENT DOCUMENTS

| | | | | |
|---|---|---|---|---|
| 3,810,465 A * | 5/1974 | Lambert | ...................... | 601/160 |
| 5,020,724 A * | 6/1991 | Kiyono et al. | ............. | 239/102.2 |
| 5,157,699 A | 10/1992 | Miyazaki et al. | | |
| 5,171,132 A | 12/1992 | Miyazaki et al. | | |
| 5,239,319 A | 8/1993 | Miyazaki et al. | | |
| 5,248,904 A | 9/1993 | Miyazaki et al. | | |
| 5,591,184 A * | 1/1997 | McDonnell et al. | ........... | 606/167 |
| 5,840,062 A * | 11/1998 | Gumaste et al. | ................ | 604/68 |
| 7,094,040 B2 | 8/2006 | Higashino et al. | | |
| 7,901,374 B2 | 3/2011 | Seto et al. | | |
| 2002/0045911 A1* | 4/2002 | Fletcher et al. | ................ | 606/167 |
| 2003/0215342 A1* | 11/2003 | Higashino et al. | ............ | 417/322 |

FOREIGN PATENT DOCUMENTS

| | | |
|---|---|---|
| JP | A-01-280694 | 11/1989 |
| JP | A-03-217672 | 9/1991 |
| JP | A-2003-500098 | 1/2003 |
| JP | A-2005-152127 | 6/2005 |
| JP | A-2005-282498 | 10/2005 |
| JP | A-2005-307777 | 11/2005 |
| WO | WO 00/71038 A1 | 11/2000 |

* cited by examiner

*Primary Examiner* — Ryan Severson
*Assistant Examiner* — Rachel S Papeika
(74) *Attorney, Agent, or Firm* — Oliff & Berridge, PLC (57) ABSTRACT

A fluid jet device being provided with a fluid jet aperture section and producing a jet of fluid from the fluid jet aperture section includes: a pulsation generation section including a fluid chamber whose capacity can be changed, an inlet fluid path linked through the fluid chamber with a volume smaller than that of the fluid chamber, and an outlet fluid path linked through the fluid chamber and the fluid jet aperture section with an inertance set smaller than that of the inlet fluid path; and a pressure generation section that supplies the fluid to the inlet fluid path.

20 Claims, 6 Drawing Sheets

FIG. 9

FLUID JET DEVICE

BACKGROUND

1. Technical Field

The present invention relates to a fluid jet device that is compact and lightweight yet produces a jet of fluid by strong high-frequency pulsation.

2. Related Art

A previous fluid jet device for use to cut open or cut and remove living body tissue is known with a fluid jet generation method of producing jets of pulsating fluid at high speed. For producing jets of fluid at high-speed as such, the fluid jet device is provided with means for flowing a fluid into a fluid chamber, and intermittently generates steam bubbles from the fluid using heating means in the fluid chamber so that the internal pressure is intermittently increased in the fluid chamber. An example includes Patent Document 1 (JP-T-2003-500098).

According to Patent Document 1, a fluid has been instantaneously heated by discharge of a high-voltage electrode or others, and utilizing the pressure generated by such heating, higher-speed jets of fluid have been produced. Thus produced jets of fluid can be used to selectively cut and remove soft tissue of living bodies during surgeries or others.

The problem with the fluid jet device of Patent Document 1 is that, however, jets of fluid coming therefrom are heated because of the configuration of producing jets of fluid by steam bubbles of the fluid. The heat may thus adversely affect any normal tissue or others. There is another problem that the actually-possible frequency for driving is about 100 Hz at the maximum because producing a jet of fluid is not allowed until the steam bubbles are disappeared.

Moreover, although Patent Document 1 describes, in the part of "Description of Exemplary Embodiments", an application example of using a piezoelectric element as jet means, but there is no description about specific implementation thereof.

The fluid jet device of Patent Document 1 has still another problem that the device cannot be available for use to remove any thrombus in blood vessels by jets of fluid directed from a fluid jet aperture section provided at the tip of a catheter, for example. This is because, for such a use, there needs to produce jets of fluid from the tip end of a thin flexible tube, but with the configuration of Patent Document 1, no pulsation can be transmitted thereby.

SUMMARY

A first aspect of the invention is directed to, characteristically, a fluid jet device including: a pulsation generation section provided with a fluid chamber whose capacity can be changed, an inlet fluid path linked through the fluid chamber with a volume smaller than that of the fluid chamber, and an outlet fluid path linked through the fluid chamber and a fluid jet aperture section with an inertance set smaller than that of the inlet fluid path; and a pressure generation section that supplies the fluid to the inlet fluid path.

In such a configuration, the pressure generation section can be a pump that discharges a fluid at any predetermined pressure, for example.

In the first aspect, because the inlet fluid path is smaller in capacity than the fluid chamber, even if a minute capacity change is observed in the fluid chamber, any effect possibly caused as a result of volume change of a gas in the fluid or the fluid itself can be minimized, thereby being able to instantaneously increase the pressure in the fluid chamber. Utilizing the increase of the pressure and the inertance difference between the inlet and outlet fluid paths, jets of fluid can be produced with efficiently-strong pulsation.

There is another effect that, by including such a pump or others for discharging a fluid at any predetermined pressure, the device can be operated stably.

In a second aspect of the invention, in the fluid jet device of the first aspect, preferably, the outlet fluid path has a length equal to or smaller than an outer diameter of a cross-sectional surface of the pulsation generation section being orthogonal to the outlet fluid path.

With such a configuration, the length of the outlet fluid path, i.e., the distance between the fluid jet aperture section and the fluid chamber, is reduced, and this thus allows transmission of pulsation generated in the fluid chamber to the fluid jet aperture section with no attenuation, thereby being able to produce jets of fluid with efficiently-strong pulsation.

In a third aspect of the invention, in the fluid jet device of the first aspect, preferably, the pulsation generation section includes a capacity change unit that changes the capacity of the fluid chamber, and the capacity change unit includes a diaphragm that seals one surface of the fluid chamber, and a piezoelectric element that is affixed to the diaphragm for deformation thereof.

With such a configuration, the capacity change unit can be a small-sized unimorph piezoelectric actuator, which is of simple configuration yet can generate high-frequency pulsation by its high-speed operation.

In a fourth aspect of the invention, in the fluid jet device of the first aspect, preferably, the pulsation generation section includes a capacity change unit that changes the capacity of the fluid chamber, and the capacity change unit includes diaphragms that respectively seal two opposing surfaces of the fluid chamber, and a piezoelectric element affixed to each of the diaphragms.

This configuration enables to, with the pulsation generation section remained small in volume, change double the capacity of the fluid chamber compared with a case where a diaphragm is configured all over the surface, thereby being able to generate pulsation at a stronger level. Contrarily, when a small capacity change will do, the resulting pulsation generation section can be smaller in size.

In a fifth aspect of the invention, in the fluid jet device of the first aspect, preferably, at least either the inlet fluid path or the outlet fluid path is a fluid hole formed to a side-wall configuring member of the fluid chamber.

Such a configuration allows to simplify the configuration of the fluid jet device with no additional component such as pipe.

In a sixth aspect of the invention, in the fluid jet device of the first aspect, preferably, at least either the inlet fluid path or the outlet fluid path is configured by a groove formed to a side-wall configuring member of the fluid chamber and a diaphragm.

With such a configuration, for forming an inlet fluid path specifically requiring to be slim and long, any desired cross-sectional area and length can be realized for the fluid path without using any special machine and tool.

In a seventh aspect of the invention, in the fluid jet device of the first aspect, preferably, at least either the inlet fluid path or the outlet fluid path is configured by a groove formed to a joint surface of two side-wall configuring members connected together on a surface substantially parallel to a diaphragm.

With such a configuration, with a groove of a semicircular cross section formed on the joint surface of the two side-wall configuring members, for example, the fluid path can be circular in shape. This favorably leads to the effect of being able to derive optimum values for the fluid path, e.g., the cross-sectional area thereof, the length thereof, and the cross-sectional shape thereof with ease.

In an eighth aspect of the invention, in the fluid jet device of the first aspect, preferably, a cover member is provided for covering the pulsation generation section.

Including a cover member as such can protect the pulsation generation section, and can also reduce any possibility of damaging a body part to be operated during surgery or others even if the tip end of the fluid jet device touches the body part.

In a ninth aspect of the invention, in the fluid jet device of the first aspect, preferably, the pulsation generation section is fixed to a tip end of a flexible tube.

Such a configuration enables a catheter-like fluid jet device provided with a small-sized pulsation generation section at the tip of a flexible tube. This accordingly enables surgery to remove thrombus or others by producing jets of fluid with the device inserted into a blood vessel.

In a tenth aspect of the invention, in the fluid jet device of the first aspect, preferably, the pulsation generation section is fixed to a tip end of a rigid pipe having a diameter substantially the same as or equal to or smaller than that of the pulsation generation section.

Such a configuration enables insertion of a tip end of the fluid jet device into any ultra-small body part for surgery by a person performing the surgery holding the upstream side of a rigid pipe.

BRIEF DESCRIPTION OF THE DRAWINGS

The invention will be described with reference to the accompanying drawings, wherein like numbers reference like elements.

DESCRIPTION OF EXEMPLARY EMBODIMENTS

In the below, embodiments of the invention are described by referring to the accompanying drawings.

Figure 5:
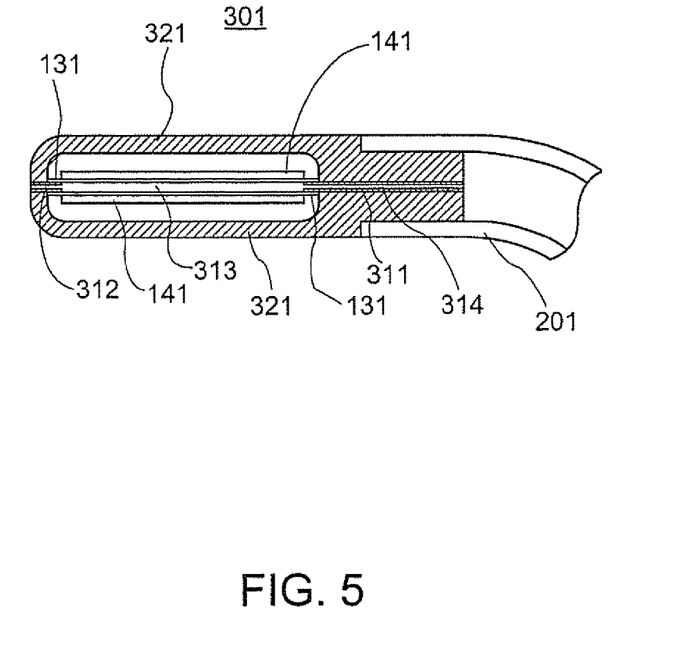
FIG. 5 is a partial cross-sectional view of a pulsation generation section of a second embodiment.
Figure 6:
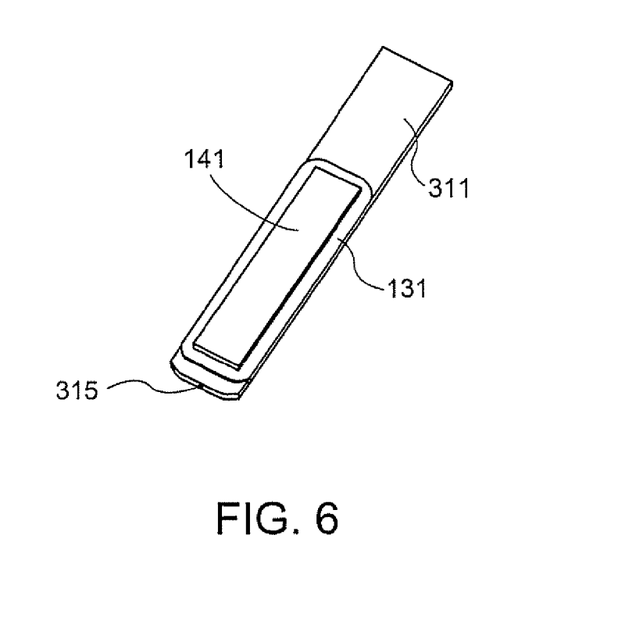
FIG. 6 is a perspective view of main components of the pulsation generation section of the second embodiment.
Figure 7:
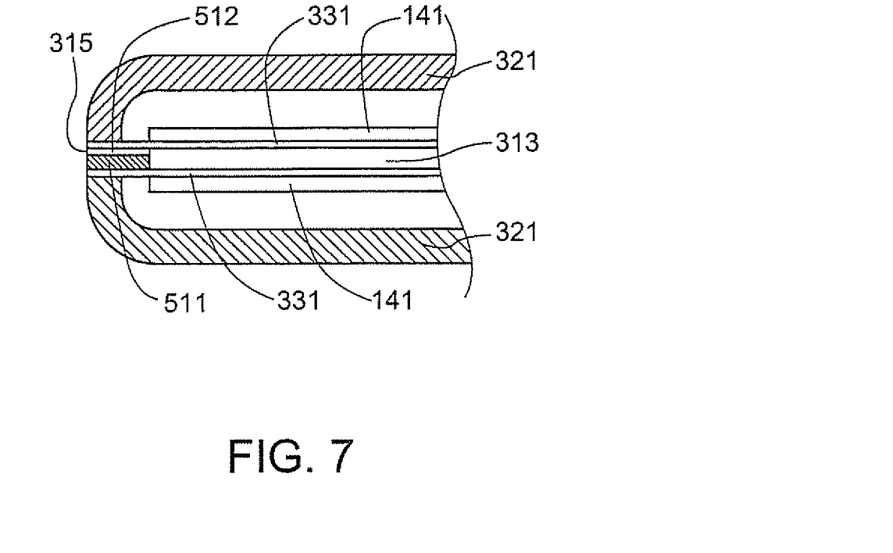
FIG. 7 is a vertical cross-sectional view of main components in a pulsation generation section of a third embodiment.
Figure 8:
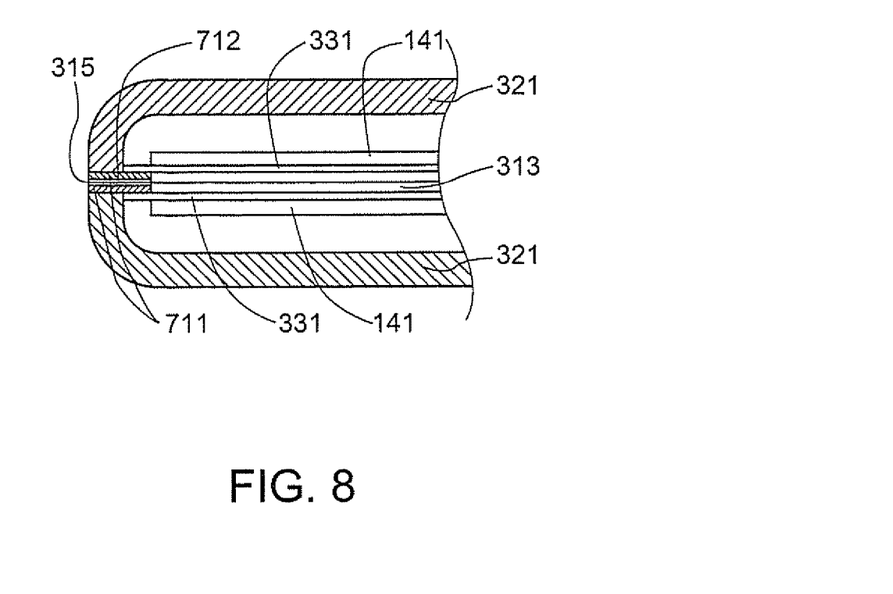
FIG. 8 is a vertical cross-sectional view of main components in a pulsation generation section of a fourth embodiment.
Figure 9:
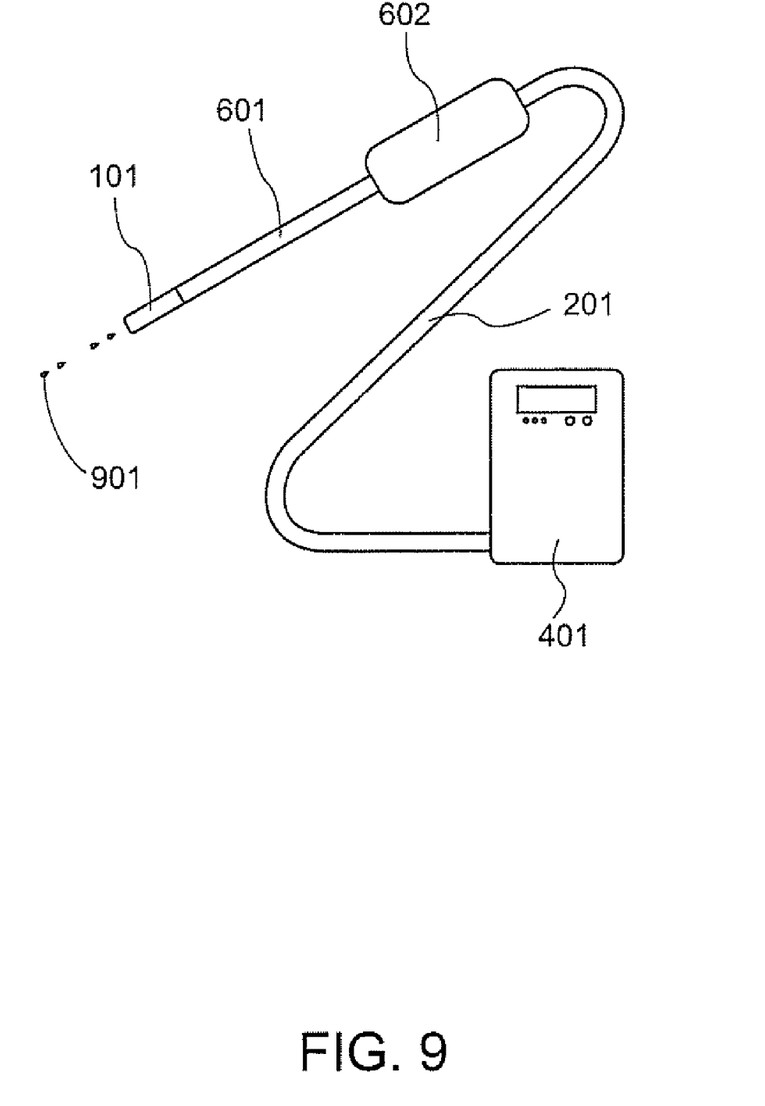
FIG. 9 is a diagram for illustrating a fluid jet device of a fifth embodiment.

FIGS. 1 to 4 each show a fluid jet device and a pulsation generation section of a first embodiment. FIGS. 5 and 6 each show a pulsation generation section of a second embodiment, FIG. 7 shows that of a third embodiment, and FIG. 8 shows that of a fourth embodiment. FIG. 9 shows a fluid jet device of a fifth embodiment.

Note that, for convenience, the drawings to be referred to in the below are those schematic with the size scale of components and sections being different from the actual.

Moreover, the fluid jet device of the embodiments of the invention is applicable to various application uses, e.g., image drawing using ink, washing of a fine object and structure, and a scalpel for surgery use. In the embodiments described below, exemplified is a fluid jet device suitable for being provided at the tip end of a catheter, which is used to remove thrombus or others through insertion into blood vessels, or a fluid jet device suitable for cutting open or cutting and removing living body tissue. Accordingly, the fluid used in the embodiments is water or a balanced saline solution.

First Embodiment

Figure 1:
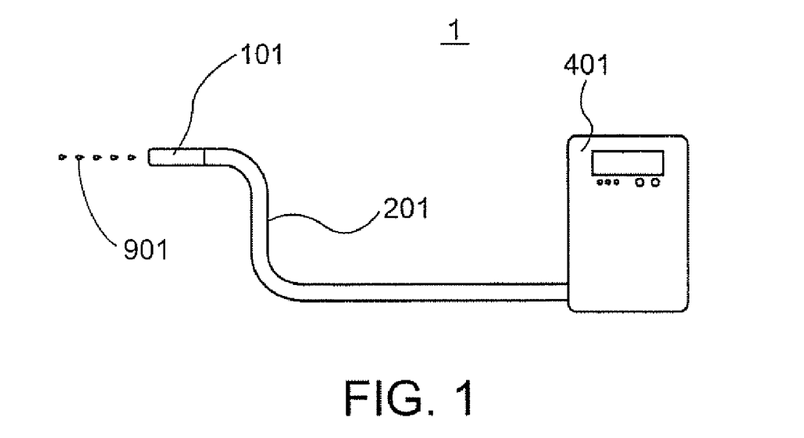
FIG. 1 is a diagram showing the schematic configuration of a fluid jet device of a first embodiment.

FIG. 1 is a diagram showing the schematic configuration of a fluid jet device of a first embodiment. In FIG. 1, a fluid jet device 1 is configured to include, basically, a pressure generation section 401, a pulsation generation section 101, and a connection tube 201. The pressure generation section 401 carries therein a fluid, and discharges the fluid at any predetermined pressure with the workings of a pump or others. The pulsation generation section 101 changes the fluid provided at the predetermined pressure as such into pulsation. The connection tube 201 is flexible, and serves to establish a connection between the pressure generation section 401 and the pulsation generation section 101. Herein, the wiring needed for driving the pulsation generation section 101 is disposed along the connection tube 201 (not shown).

Figure 2:
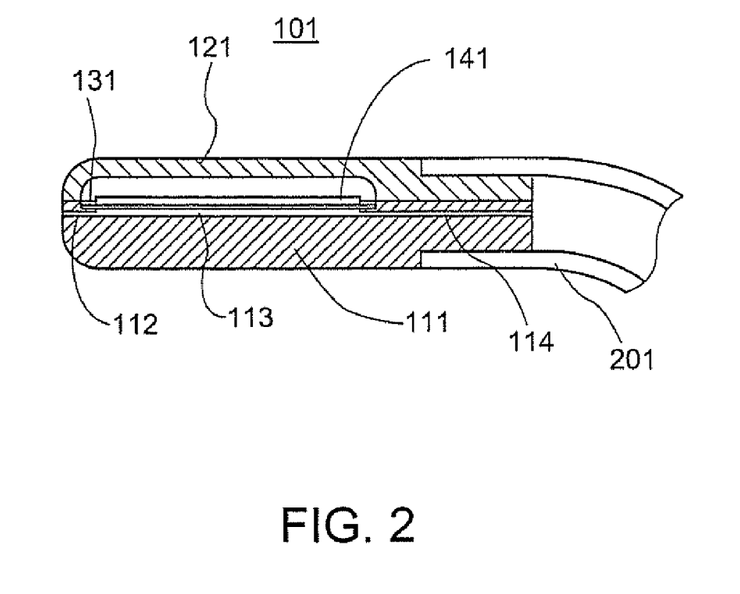
FIG. 2 is a vertical cross-sectional view of a pulsation generation section of the first embodiment.
Figure 3:
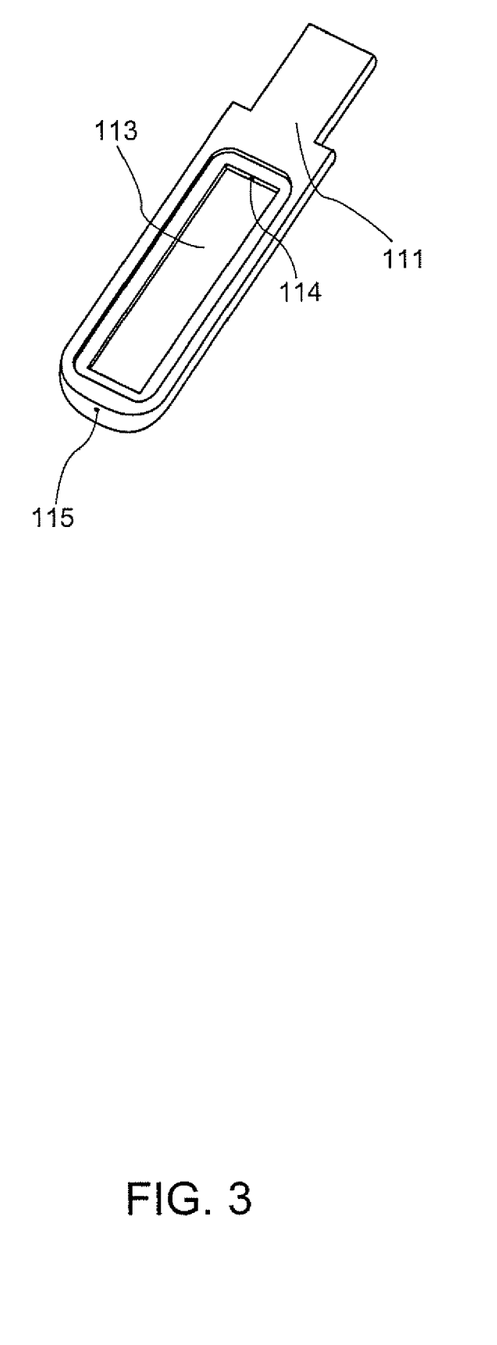
FIG. 3 is a perspective view of a fluid path forming member in the pulsation generation section of the first embodiment.

Described next is the pulsation generation section 101 of the first embodiment by referring to FIGS. 2 to 4. FIG. 2 is a vertical cross-sectional view of the pulsation generation section in the fluid jet device of the first embodiment of the invention. FIG. 3 is a perspective view of a fluid path forming member, and FIG. 4 is a perspective view of main components in the pulsation generation section.

In FIGS. 2 and 3, the pulsation generation section 101 is provided with a fluid path forming member 111 formed with a concave portion configuring a fluid chamber 113. Herein, the fluid path forming member 111 configures a side wall of the fluid chamber 113, i.e., a side-wall configuring member. The fluid path forming member 111 configuring a side wall of the fluid chamber 113 as such is drilled with an inlet fluid path 114. As to this inlet fluid path 114, one end thereof is linked through the fluid chamber 113, and the other end thereof is linked through the connection tube 201. In the fluid chamber 113, on the side wall opposite to the side wall drilled with the inlet fluid path 114 as such, an outlet fluid path 112 is drilled. As to the outlet fluid path 112, one end thereof is linked through the fluid chamber 113, and the other end thereof is linked through the outside of the fluid chamber 113. One of the two ends of the outlet fluid path 112, i.e., one end linked through the outside of the fluid chamber 113, serves as a fluid jet aperture section 115, from which jets of fluid are directed. This outlet fluid path 112 has the length set to be sufficiently smaller than the maximum outer diameter of the pulsation generation section 101.

Figure 4:
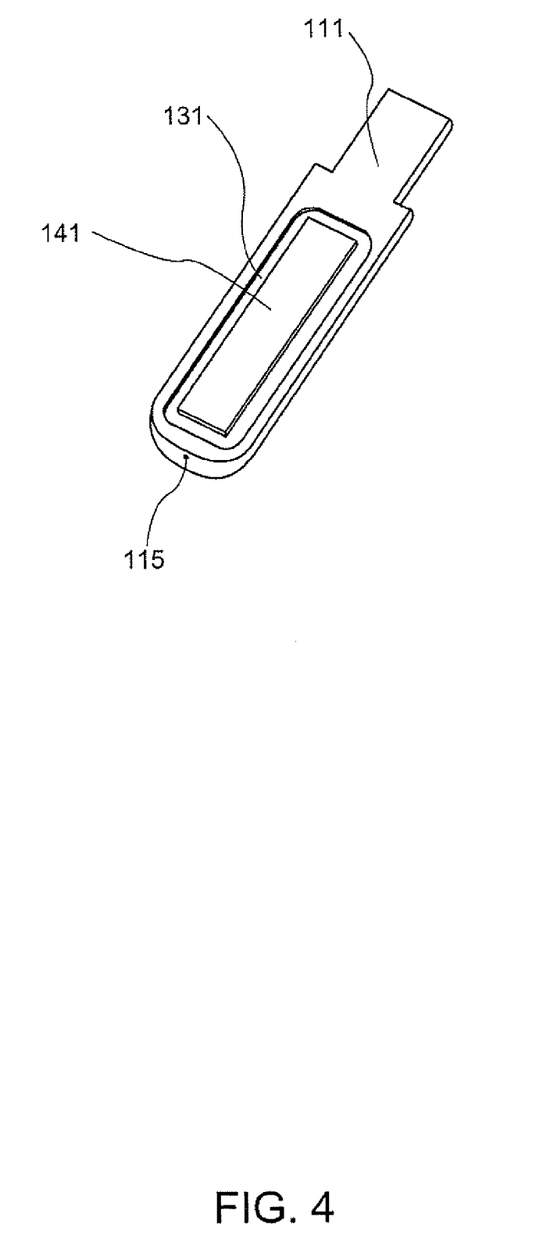
FIG. 4 is a perspective view of main components in the pulsation generation section of the first embodiment.

In FIGS. 2 and 4, one surface of the fluid chamber 113 is sealed by a diaphragm 131. The diaphragm 131 is affixed in advance with a piezoelectric element 141. This piezoelectric element 141 uses the diaphragm 131 as an electrode, and on the surface opposing thereto, an electrode member (not shown) is formed for use as an electrode of opposite polarity. The wiring from these electrodes is disposed along the connection tube 201 as described above (not shown). The fluid path forming member 111 is affixed with a cover member 121 with enough space not to disturb the operation of the diaphragm 131 and that of the piezoelectric element 141.

Next, described briefly is the flow of a fluid in the fluid jet device 1. The pressure generation section 401 carries therein a fluid container, and a pump connected to the fluid container (both are not shown). The pump is so connected as to direct a fluid to the connection tube 201. The fluid stored in the fluid container is provided by the pump to the inlet fluid path 114 at a constant pressure via the connection tube 201. The fluid is then discharged from the fluid jet aperture section 115 via the fluid chamber 113 and the outlet fluid path 112. Note here that, when the piezoelectric element 141 is not driven, the fluid discharge is made in a sequential manner at a slow speed.

By referring to FIGS. 1 to 4, described next is the operation in this embodiment. From the pulsation generation section 101 in this embodiment, fluid discharge is made utilizing a difference between an inertance L1 on the inlet fluid path side, i.e., referred also to as combined inertance L1 on the inlet fluid path side, and an inertance L2 on the outlet fluid path side, i.e., referred also to as combined inertance L2 on the outlet fluid path side.

Described first is the inertance.

The inertance L is expressed by $L=\rho \times h/S$, where the fluid density is $\rho$, the cross-sectional area of the fluid path is S, and the length of the fluid path is h. Assuming that the pressure difference between the fluid path and another is $\Delta P$, and the quantity of flow of the fluid flowing through the fluid path is Q, the relationship of $\Delta P=L \times dQ/dt$ can be derived by modifying the equation of motion in the fluid path using the inertance L.

That is, the inertance L denotes the degree of influence over the temporal change of the quantity of flow. The larger inertance L leads to the smaller temporal change of the quantity of flow, and the smaller inertance L leads to the larger temporal change of the quantity of flow.

The combined inertance related to the parallel connection of a plurality of fluid paths and the series connection of a plurality of different-shaped paths can be calculated by combining together the inertance of each of the paths similarly to the parallel or series connection of inductances in an electric circuit.

Note that, because the connection tube 201 is made flexible for establishing a connection between the pressure generation section 401 and the inlet fluid path, the tube may be eliminated from the calculation of the inertance L1 on the inlet fluid path side.

In this embodiment, settings related to the inlet and outlet fluid paths 114 and 112 are so made that the inertance L1 on the inlet fluid path side becomes larger than the inertance L2 on the outlet fluid path side. The settings include the length and the cross-sectional area of the inlet fluid path 114, and those of the outlet fluid path 112.

Described next is the operation of the pulsation generation section 101.

With the workings of the pressure generation section 401, the inlet fluid path 114 is provided with a fluid always at a constant fluid pressure. With such a fluid supply, when the piezoelectric element 141 is not operating, by the fluid resistance in the components, i.e., the inlet fluid path 114, the fluid chamber 113, and the outlet fluid path 112, and the above-described fluid pressure, the fluid flows out from the fluid jet aperture section 115. This flow-out of the fluid is very slow, thereby not being able to cut open or cut and remove human body tissue.

Assuming here is a case where the piezoelectric element 141 is provided with a drive signal, and the piezoelectric element 141 is resultantly compressed quickly. If this is the case, the diaphragm 131 is quickly bent into a convex shape in the direction of reducing the volume of the fluid chamber 113. As a result, the pressure in the fluid chamber 113 is rapidly increased and reaches a pressure of several atmospheres if the inertances L1 and L2 on the sides of the inlet and outlet fluid paths are large enough.

This pressure is much larger than the pressure having been applied to the inlet fluid path 114 by the pressure generation section 401. Accordingly, due to the pressure, the fluid flow from the inlet fluid path side to the fluid chamber 113 is reduced, and the fluid flow from the outlet fluid path 112 is increased. However, because the inertance L1 on the side of the inlet fluid path 114 is larger than the inertance L2 on the side of the outlet fluid path 112, the degree of increase of the fluid flow from the side of the outlet fluid path 112 is larger than the degree of reduction of the fluid flow from the side of the inlet fluid path 114 into the fluid chamber 113.

This makes fluid discharge to be pulse-like from the fluid jet aperture section 115 through the outlet fluid path 112, i.e., produces jets of pulse-like fluid 901 at high speed.

With the interaction between the quantity reduction of the fluid flow from the inlet fluid path 114 and the quantity increase thereof from the outlet fluid path 112, immediately after the increase of pressure, the fluid chamber 113 is reduced in pressure or is put under vacuum. As a result, after a fixed length of time, the flow velocity of the fluid in the inlet fluid path 114 is put back to the value similarly before the operation of the piezoelectric element 141 by the pressure of the pressure generation section 401 and the fluid chamber 113 being low in pressure or vacuum. After the fluid flow is recovered in the inlet fluid path 114, if the piezoelectric element 141 is being compressed, jets of pulse-like fluid can be successively produced at high speed from the fluid jet aperture section 115.

As such, according to the first embodiment described above, with the workings of the pressure generation section 401, the inlet fluid path 114 in the pulsation generation section 101 is stably provided with a fluid at a constant pressure. Accordingly, there is no more need for priming or others in the initial operation, and right after the device is activated, jets of fluid can be produced with any desired amount.

The supply of pressure from the pressure generation section 401 is generally set to be of a pressure of 1 atmosphere or lower (0.1 Mpa), and preferably, a pressure of 0.3 atmospheres or lower (0.03 MPa). When the fluid jet device 1 is provided at the tip end of a catheter, for example, the pulsation generation section 101 is required to be inserted along a blood vessel. In this sense, the connection tube 201 is preferably as flexible as possible. For such flexibility, preferably, any thin tube is used, and the pressure in the tube is reduced within a range that allows fluid transmission to the pulsation generation section 101. For such pressure reduction, there needs to set minimum the resistance in the fluid paths, i.e., the inlet fluid path 114, the fluid chamber 113, and the outlet fluid path 112.

Moreover, when a device failure might possibly cause a serious accident especially if the device is used for a brain surgery or provided to a catheter, any possibility of producing jets of high-pressure fluid due to splitting of the connection tube 201 or others has to be avoided without fail. Also in this respect, the connection tube 201 is required to be low in pressure.

When the fluid jet device 1 is used for a brain surgery being required to cut and remove very small body parts, for example, the pulsation generation section 101 preferably has the diameter of 3 mm or smaller, preferably 2 mm or smaller. When the fluid jet device 1 is provided to a catheter, for example, the diameter thereof is 2 mm or smaller, preferably 1 mm or smaller. The pulsation generation section 101 is also required to have the length of 20 mm or shorter, preferably 10 mm or shorter not to hinder flexible bend of the catheter.

With such a small diameter, the diaphragm 131 and the piezoelectric element 141 can be considerably reduced in size, i.e., preferably, the area of the diaphragm 131 contributing the capacity change of the fluid chamber 113 is approximately 20-square millimeters or smaller, generally 10-square millimeters or smaller, and the displacement amount thereof is preferably 100 μm or smaller.

Accordingly, for effectively using such a minute volume change to produce jets of fluid, there needs to increase the amount of fluid flowing out from the outlet fluid path 112 compared with the decreasing amount of fluid flowing from the inlet fluid path side into the fluid chamber 113. In consideration thereof, the inertance L1 of the inlet fluid path 114 is set larger than the inertance L2 of the outlet fluid path 112, and the ratio of the inertance L1 to the inertance L2 is 5:1 or more, preferably 10:1 or more.

By the volume of the inlet fluid path 114 set smaller as such than that of the fluid chamber 113, any possible loss to be caused by the minute capacity change observed in the fluid chamber 113 can be reduced thanks to the compression as a result of pressure increase of the fluid in the inlet fluid path 114, the capacity increase as a result of deformation of components around the inlet fluid path 114, and others.

The length of the outlet fluid path 112, i.e., the path length from the fluid jet aperture section 115 to the fluid chamber 113, is set equal to or smaller than the maximum diameter of the pulsation generation section 101. This is because, as described above, the amount of capacity change of the fluid chamber 113 varies in accordance with the maximum outer diameter of the pulsation generation section so that, for the pulsation generation section having the smaller maximum outer diameter, the outlet fluid path is required to be shorter in length to lead to a smaller loss.

Generally, the length of the outlet fluid path 112 is set specifically to 1 mm or smaller, preferably 0.5 mm or smaller. With such a setting, the distance between the fluid jet aperture section 115 and the fluid chamber 113 is reduced, thereby being able to transmit pulsation generated in the fluid chamber to the fluid jet aperture section 115 with no attenuation thereof. Accordingly, the jets of fluid can be directed with efficiently strong pulsation. Moreover, setting shorter the length of the outlet fluid path 112 leads to reduction of the inertance L2 of the outlet fluid path 112 described above, thereby being able to produce jets of fluid with more efficiency.

Alternatively, the cross-sectional area of the fluid jet aperture section 115 may be set smaller than that of the outlet fluid path 112. If this is the configuration, the jets of fluid can be directed from the fluid jet aperture section 115 at higher speed without increasing the resistance of the outlet fluid path and the inertance thereof. For brain surgeries or others, there are advantages of being able to produce smaller-diameter jets of fluid, thereby being able to perform more precise surgeries.

With the configuration of using the piezoelectric element 141 and the diaphragm 131 as a capacity change unit, the resulting configuration can be simplified, and the device can be accordingly reduced in size. This also allows the maximum frequency of capacity change in the fluid chamber 113 to be higher, i.e., 1 to 10 KHz or more, and this is considered ideal for producing jets of pulsating fluid at high speed.

Also with the configuration that the inlet and outlet fluid paths 114 and 112 are respectively formed to the side walls of the fluid chamber 113, the number of components is not increased. What is more, the area around the diaphragm 131 can be formed smooth with the surface fixed with the fluid path forming member 111, thereby being able to seal the fluid chamber 113 without fail. For fixing together the diaphragm 131 and the fluid path forming member 111, various methods are possible, e.g., adhesion, laser welding of area therearound, and diffusion bonding.

In this embodiment, the fluid chamber 113 formed to serve as a concave portion of the fluid path forming member 111 is shaped like a rectangular parallelepiped. Alternatively, the corner portions of the fluid chamber 113 may be rounded, and if this is the configuration, the increase of durability can be expected because bubble condensation can be reduced and stress concentration to the diaphragm can be relaxed.

Second Embodiment

Described next is a fluid jet device of a second embodiment by referring to the accompanying drawings.

In the second embodiment, diaphragms each affixed with a piezoelectric element are disposed to oppose each other with a fluid chamber sandwiched therebetween, and the diaphragms serve to seal the fluid chamber. With such a configuration, the fluid chamber can remain small in size but the capacity change thereof can be large, thereby being able to produce jets of fluid with more intensity. Herein, any component similar to that in the first embodiment is provided with the same reference numeral and described, and any operation similar thereto is not described twice.

FIG. 5 is a partial cross-sectional view of a pulsation generation section of the second embodiment, and FIG. 6 is a perspective view of main components of the pulsation generation section.

In FIGS. 5 and 6, a pulsation generation section 301 is provided with a fluid path forming plate 311, which is made of highly-corrosive resistive metal such as stainless steel, or made of ceramic, for example. The fluid path forming plate 311 is formed with a through hole configuring a fluid chamber 313 in the thickness direction. In this embodiment, the fluid path forming plate 311 is a side-wall configuring member that configures a side wall of the fluid chamber 313. The fluid path forming plate 311 configuring the side wall of the fluid chamber 313 as such is formed with an inlet fluid path 314. The inlet fluid path 314 is so formed as to be substantially parallel to the plate surface of the fluid path forming plate 311, and an end thereof is linked through the fluid chamber 313, and the other end thereof is linked through the connection tube 201. In the fluid chamber 313, the side wall opposing the side wall drilled with the inlet fluid path 314 is drilled with an outlet fluid path 312. As to the outlet fluid path 312, an end is linked through the fluid chamber 313, and the other end is linked through the outside of the fluid chamber 313. One of the two ends of the outlet fluid path 312, i.e., one end linked through the outside of the fluid chamber 313, serves as a fluid jet aperture section 315, from which jets of fluid are directed.

The fluid path forming plate 311 is so set as to have the thickness falling within a range from 0.1 mm to 1 mm inclusive for allowing formation therein of inlet and outlet fluid paths each having the diameter of 0.05 mm or larger, and for keeping the fluid sufficiently for a small capacity change in the pressure chamber and for keeping the rigidity of the fluid chamber.

To the both surfaces of the fluid path forming plate 311, the diaphragm 131 is each fixed, thereby sealing the fluid chamber 313. On the surface of each of the diaphragms 131 located opposite to the fluid chamber 313, the piezoelectric element 141 is affixed. This piezoelectric element 141 uses the diaphragm 131 as an electrode, and on the surface opposing the diaphragm 131, an electrode member is formed for use as an electrode on the other side. The wiring from the diaphragm 131 is coupled with the wiring from the electrode member, and the resulting wiring is disposed along the connection tube 201 (not shown).

On the both surfaces of the fluid path forming plate 311, a cover member 321 is each provided with a sufficient space therefrom not to disturb the movement of the diaphragms 131 and that of the piezoelectric elements 141. The cover member 321 serves to seal and protect the piezoelectric elements 141 or others from the outside, and to provide a safety when a tip end of the device touches any body part to be operated during a surgery.

Described next is the operation of the pulsation generation section 301 configured as such. Similarly to the first embodiment, the inlet fluid path 314 is provided with a fluid always at a constant pressure from a pressure generator. Assuming here is a case where the piezoelectric elements 141 are each provided with a drive signal, and the piezoelectric elements 141 are resultantly compressed quickly. If this is the case, the diaphragms 131 on the both surfaces of the fluid chamber 313 are each quickly bent into a convex shape in the direction of reducing the volume of the fluid chamber 313. As a result, the pressure in the fluid chamber 313 is rapidly increased and reaches a pressure of several atmospheres if the inertances L1 and L2 on the sides of the inlet and outlet fluid paths are large enough.

This pressure is much larger than the pressure having been applied to the inlet fluid path 314 by the pressure generation section 401. Accordingly, due to the pressure, the fluid flow from the inlet fluid path side to the fluid chamber 313 is reduced, and the fluid flow from the outlet fluid path 312 is increased. However, because the inertance L1 on the side of the inlet fluid path 314 is larger than the inertance L2 on the side of the outlet fluid path 312, the degree of increase of the fluid flow from the side of the outlet fluid path 312 is larger than the degree of reduction of the fluid flow from the side of the inlet fluid path 314 to the fluid chamber 313.

With such an operation, the diaphragms 131 in the second embodiment reduce the capacity of the fluid chamber 313 from the both sides thereof, thereby allowing a large capacity change, and also allowing jets of fluid to be produced with stronger pulsation compared with the first embodiment.

Moreover, when the same level of jet intensity as the first embodiment will do for the pulsating fluid, the diaphragms can be reduced in area to a further degree, thereby being able to reduce the size of the pulsation generation section. Such a size reduction favorably leads to a wider range of uses, e.g., allows surgeries in narrower blood vessels when the pulsation generation section is provided at the tip of a catheter. What is better, the resulting fluid jet device can be more suitable for a brain surgery or others being required to cut and remove very small body parts.

Third Embodiment

Described next is a third embodiment by referring to the accompanying drawings. In the third embodiment, characteristically, at least either the inlet or outlet fluid path is configured by a groove portion formed to a fluid path forming plate and a diaphragm.

FIG. 7 is a vertical cross-sectional view of main components in a pulsation generation section of the third embodiment. The configuration of the third embodiment other than the inlet and outlet fluid paths is the same as that in the second embodiment described above, and thus is not described again. In the third embodiment, any component similar to that in the second embodiment is provided with the same reference numeral and described.

Similarly to the second embodiment, a fluid path forming plate 511 is formed with a through hole in the thickness direction, thereby forming the fluid chamber 313. On one surface of the fluid path forming plate 511, a U-shaped groove portion is provided for forming an outlet fluid path 512. An inlet fluid path is also similarly formed (not shown). By fixing a diaphragm 331 to the fluid path forming plate 511, the upper surface of the U-shaped groove portion is sealed so that the outlet fluid path 512 is formed.

The groove portion is not necessarily shaped like the letter U, and may be shaped like a rectangle or an arc, for example. However, for preventing bubble condensation as much as possible, the groove portion preferably has the cross section of a shape whose corner portions are round and smooth if possible. This third embodiment is surely applicable also to the configuration of the above-described first embodiment by forming a groove to the fluid path forming member.

This configuration of this embodiment requires no processing of an inlet fluid path having the small cross-sectional area using any special drill or others, thereby being able to configure a fluid jet device with ease.

Fourth Embodiment

Described next is a fourth embodiment by referring to the accompanying drawings. In the fourth embodiment, characteristically, the fluid path forming plate in the second embodiment described above is configured by two component parts, which are results of partitioning the plate into two in the thickness direction, and at least either an inlet or outlet fluid path is configured by a groove portion formed to the joint surface of the two component parts, i.e., the fluid path forming plates.

FIG. 8 is a vertical cross-sectional view of main components in a pulsation generation section of the fourth embodiment. The configuration of the fourth embodiment other than the inlet and outlet fluid paths is the same as that in the second embodiment described above, and thus is not described again. In the fourth embodiment, any component similar to that in the second embodiment is provided with the same reference numeral and described.

Similarly to the second embodiment, two fluid path forming plates 711 are each formed with a through hole in the thickness direction, and these two fluid path forming plates 711 are attached to each other, thereby forming the fluid chamber 313. The surfaces of the fluid path forming plates 711 for attachment are each provided with a groove portion having the semi-circular cross section, and when the plates are attached together, an outlet fluid path 712 having the circular cross-section is formed. An inlet fluid path is also similarly formed (not shown).

This configuration of this embodiment leads to an effect of being able to easily form inlet and outlet fluid paths of any arbitrary shape not using a special drill or others but only by forming a groove portion to each of the fluid path forming plates 711. Moreover, the fourth embodiment can be applicable also to the configuration of the first embodiment as a combination of the groove-formed fluid path forming member and the groove-formed fluid path forming plate.

Fifth Embodiment

Described next is a fifth embodiment of the invention by referring to the accompanying drawings. In the fifth embodiment, characteristically, the pulsation generation section is fixed to a tip end of a rigid pipe having the diameter substantially the same as or smaller than that of the pulsation generation section. The internal configuration and operation of the pulsation generation section not including the fixing method of the pulsation generation section are the same as those in the first to fourth embodiments described above, and thus are not described again.

FIG. 9 is a diagram for illustrating a fluid jet device of the fifth embodiment. In FIG. 9, the flexible connection tube 201 receiving a fluid from the pressure generation section 401 is connected to a rigid tube 601 in a grip section 602. This rigid tube 601 has the diameter substantially the same as or smaller than that of the pulsation generation section 101. From the pulsation generation section 101, the jets of pulse-like fluid 901 are produced at high speed.

As such, in this embodiment, a fluid jet aperture section can be directed to any arbitrary direction, and the rigid tube 601 has the diameter same as or smaller than that of the pulsation generation section 101, thereby easing a brain surgery being required to cut and remove very small body parts. Moreover, if the rigid tube 601 is manufactured using a metal or a composite material of resin and metal, the rigid tube 601 can be arbitrarily bent in accordance with a body part to be operated to make it suitable for operating a surgery.

The entire disclosure of Japanese Patent Application No. 2007-208960, filed Aug. 10, 2007, is expressly incorporated by reference herein.

What is claimed is:

1. A fluid jet device that is provided with a fluid jet aperture section and produces a jet of fluid that is ejected from the device into an ambient pressure environment at an exit aperture that is formed in the fluid jet aperture section, the device comprising:
    a pulsation generation section including (i) a fluid chamber whose capacity can be changed, (ii) an inlet fluid path having an upstream path end and a downstream path end, the downstream path end of the inlet fluid path being adjacent to and opening into the fluid chamber, the inlet fluid path having a total volume smaller than that of the fluid chamber, (iii) an outlet fluid path having an upstream path end and a downstream path end, the upstream path end of the outlet fluid path being adjacent to and opening into the fluid chamber and the downstream path end terminating at the exit aperture of the fluid jet aperture section, the outlet fluid path having an inertance that is smaller than that of the inlet fluid path, (iv) a first sidewall configuring member defining a first sidewall of the fluid chamber that extends in a direction parallel to the primary direction of fluid flow through the fluid chamber, (v) a second sidewall configuring member defining a second sidewall of the fluid chamber that extends in the direction parallel to the primary direction of fluid flow through the fluid chamber, and (vi) a diaphragm that defines another wall of the fluid chamber, wherein at least either the inlet fluid path or the outlet fluid path comprises a fluid pathway that is defined by a surface of the first sidewall configuring member, and wherein the surface of the first sidewall configuring member and a surface of the second sidewall configuring member are substantially parallel to the diaphragm, and the surface of the first sidewall configuring member abuts the surface of the second sidewall configuring member; and
    a pressure generation section that supplies the fluid to the inlet fluid path;
    wherein inertance L is defined as $$L = \rho \times h / S$$

where $\rho$ is fluid density, h is fluid path length, and S is fluid path cross-sectional area.

2. The fluid jet device according to claim 1, wherein the outlet fluid path has a total length equal to or smaller than an outer diameter of a cross-sectional surface of the pulsation generation section being orthogonal to the outlet fluid path.

3. The fluid jet device according to claim 1, wherein the pulsation generation section includes a capacity change unit that changes the capacity of the fluid chamber, and the capacity change unit includes the diaphragm, which seals one surface of the fluid chamber, and a piezoelectric element that is affixed to the diaphragm for deformation thereof.

4. The fluid jet device according to claim 1, wherein the pulsation generation section includes a capacity change unit that changes the capacity of the fluid chamber, and the capacity change unit includes the diaphragm and another diaphragm that respectively seal two opposing surfaces of the fluid chamber, and a piezoelectric element affixed to each of the diaphragms.

5. The fluid jet device according to claim 1, wherein at least either the inlet fluid path or the outlet fluid path comprises a fluid pathway that is defined by both the first sidewall configuring member and the diaphragm.

6. The fluid jet device according to claim 1, further comprising a cover member that covers the pulsation generation section.

7. The fluid jet device according to claim 1, wherein the pulsation generation section is fixed to a tip end of a flexible tube.

8. The fluid jet device according to claim 1, wherein the pulsation generation section is fixed to a tip end of a rigid pipe having a diameter substantially the same as or equal to or smaller than that of the pulsation generation section.

9. The fluid jet device according to claim 1, wherein a ratio of the inertance of the inlet fluid path to the inertance of the outlet fluid path is 5:1 or more.

10. The fluid jet device according to claim 1, wherein a ratio of the inertance of the inlet fluid path to the inertance of the outlet fluid path is 10:1 or more.

11. The fluid jet device according to claim 1, wherein the total length of the outlet fluid path is 1 mm or less.

12. The fluid jet device according to claim 1, wherein the total length of the outlet fluid path is 0.5 mm or less.

13. A fluid jet device that produces a jet of fluid that is ejected from the device into an ambient pressure environment, the device comprising:
    a pulsation generation section that includes:
        a fluid chamber with (i) a sidewall, a top wall and a bottom wall, each of which has a dimension extending in a direction parallel to a primary direction of fluid flow in the fluid chamber, (ii) a rigid member defining the sidewall, and (iii) two flexible diaphragms that respectively define the top wall and the bottom wall of the fluid chamber, wherein the fluid chamber has a capacity that can be changed when the diaphragms are flexed;
        a rigid inlet fluid path having an upstream path end and a downstream path end, the downstream path end of the inlet fluid path being adjacent to and opening into the fluid chamber; and
        an outlet fluid path having an upstream path end and a downstream path end, the upstream path end of the outlet fluid path being adjacent to and opening into the fluid chamber, and the downstream path end terminating at an exit aperture that coincides with the location where the jet of fluid is ejected from the device into the ambient pressure environment; and
    a pressure generation section that supplies the fluid to the inlet fluid path;
    wherein:
        (i) the outlet fluid path has an inertance that is at least 5 times smaller than the inertance of the inlet fluid path, the inertance L being defined as $$L = \rho \times h / S$$

where ρ is fluid density, h is fluid path length, and S is fluid path cross-sectional area, and (ii) the inlet fluid path has a total volume that is smaller than that of the fluid chamber.

14. The fluid jet device according to claim 13, wherein at least one of the inlet fluid path and the outlet fluid path is formed in the rigid member.

15. The fluid jet device according to claim 14, wherein both of the inlet fluid path and the outlet fluid path are formed in the rigid member.

16. The fluid jet device according to claim 13, wherein the rigid member at least partially defines the inlet fluid path, the outlet fluid path and the sidewall of the fluid chamber.

17. The fluid jet device according to claim 16, wherein the rigid member is a single unitary structure that continuously extends at least from the upstream path end of the inlet fluid path to the downstream path end of the outlet fluid path.

18. The fluid jet device according to claim 13, wherein the rigid member forms a space that defines a perimeter of the fluid chamber.

19. The fluid jet device according to claim 13, wherein the rigid member forms a rectangular space that defines a perimeter of the fluid chamber.

20. The fluid jet device according to claim 13, wherein the outlet fluid path has an inertance that is at least 10 times smaller than the inertance of the inlet fluid path.

* * * * *

UNITED STATES PATENT AND TRADEMARK OFFICE
CERTIFICATE OF CORRECTION

| | |
|---|---|
| PATENT NO. | : 8,308,745 B2 |
| APPLICATION NO. | : 12/184646 |
| DATED | : November 13, 2012 |
| INVENTOR(S) | : Takeshi Seto et al. |

It is certified that error appears in the above-identified patent and that said Letters Patent is hereby corrected as shown below:

Title Page, Item 75 should read Takeshi Seto.

Signed and Sealed this
Nineteenth Day of March, 2013

Teresa Stanek Rea
*Acting Director of the United States Patent and Trademark Office*